US010111753B2

(12) United States Patent
Patterson et al.

(10) Patent No.: US 10,111,753 B2
(45) Date of Patent: Oct. 30, 2018

(54) ADDITIVE AND SUBTRACTIVE MANUFACTURING PROCESS FOR PRODUCING IMPLANTS WITH HOMOGENEOUS BODY SUBSTANTIALLY FREE OF PORES AND INCLUSIONS

(71) Applicant: Titan Spine, LLC, Mequon, WI (US)

(72) Inventors: Chad J. Patterson, Port Washington, WI (US); Jennifer M. Schneider, Germantown, WI (US); Mark E. Berg, Fort Wayne, IN (US)

(73) Assignee: Titan Spine, Inc., Mequon, WI (US)

( * ) Notice: Subject to any disclaimer, the term of this patent is extended or adjusted under 35 U.S.C. 154(b) by 569 days.

(21) Appl. No.: 14/719,387

(22) Filed: May 22, 2015

(65) Prior Publication Data

US 2015/0335434 A1 Nov. 26, 2015

Related U.S. Application Data

(60) Provisional application No. 62/002,243, filed on May 23, 2014.

(51) Int. Cl.
*A61F 2/28* (2006.01)
*A61F 2/30* (2006.01)
(Continued)

(52) U.S. Cl.
CPC ............ *A61F 2/30767* (2013.01); *A61F 2/28* (2013.01); *B23K 15/00* (2013.01);
(Continued)

(58) Field of Classification Search
CPC .......................... B23K 15/00; B23K 15/0086; B23K 15/0093; B23K 26/00; B23K 26/0015;
(Continued)

(56) References Cited

U.S. PATENT DOCUMENTS

| 5,787,965 A | 8/1998 | Sterett et al. |
| 6,068,043 A | 5/2000 | Clark |

(Continued)

FOREIGN PATENT DOCUMENTS

| WO | 2007045471 | 4/2007 |
| WO | 2013124576 | 8/2013 |

(Continued)

OTHER PUBLICATIONS

Shellabear, M., et al., "DMLS-Development History and State of the Art", LANE Conference, 2004, Erlangen, Germany.
(Continued)

*Primary Examiner* — Veronica F Faison
(74) *Attorney, Agent, or Firm* — Stradley Ronon Stevens & Young, LLP

(57) ABSTRACT

Implants are formed from a multiple staged process that combines both additive and subtractive techniques. Additive techniques melt powders and fragments of a desired material, then successively layer the molten material into the desired implant shape, without compressing or remelting for homogenization of the layers, thereby producing an implant that is substantially free of pores and inclusions. Subtractive techniques refine implant surfaces to produce a bioactive roughened surface comprised of macro, micro, and nano structural features that facilitate bone growth and fusion.

24 Claims, 8 Drawing Sheets

(51) Int. Cl.
*B23K 15/00* (2006.01)
*B23K 26/34* (2014.01)
*B23K 26/00* (2014.01)
*C23F 1/16* (2006.01)
*B33Y 10/00* (2015.01)
*B33Y 80/00* (2015.01)
*C23F 1/26* (2006.01)

(52) U.S. Cl.
CPC ...... *B23K 15/0086* (2013.01); *B23K 15/0093* (2013.01); *B23K 26/00* (2013.01); *B23K 26/0015* (2013.01); *B23K 26/34* (2013.01); *B23K 26/345* (2013.01); *C23F 1/16* (2013.01); *A61F 2002/3084* (2013.01); *A61F 2002/3097* (2013.01); *A61F 2002/30925* (2013.01); *A61F 2002/30985* (2013.01); *B33Y 10/00* (2014.12); *B33Y 80/00* (2014.12); *C23F 1/26* (2013.01)

(58) Field of Classification Search
CPC ...... B23K 26/34; B23K 26/345; B33Y 10/00; B33Y 80/00; A61F 2002/3084; A61F 2002/30925; A61F 2002/3097; A61F 2002/30985; A61F 2/28; A61F 2/30767
See application file for complete search history.

(56) References Cited

U.S. PATENT DOCUMENTS

| | | |
|---|---|---|
| 7,079,914 B2 | 7/2006 | Berggren |
| 7,166,129 B2 | 1/2007 | Michelson |
| 7,241,313 B2 | 7/2007 | Unwin et al. |
| 7,497,876 B2 | 5/2009 | Tuke et al. |
| 7,537,664 B2 | 5/2009 | O'Neill et al. |
| 8,052,743 B2 | 11/2011 | Weber et al. |
| 8,350,186 B2 | 1/2013 | Jones et al. |
| 8,409,655 B2 | 4/2013 | Fischer et al. |
| 8,444,914 B2 | 5/2013 | Fecher et al. |
| 8,454,705 B2 | 6/2013 | Pressacco et al. |
| 8,590,157 B2 | 11/2013 | Kruth et al. |
| 2003/0065400 A1 | 4/2003 | Beam et al. |
| 2004/0153154 A1 | 8/2004 | Dinkelacker |
| 2007/0118243 A1* | 5/2007 | Schroeder .......... A61B 17/8061 700/118 |
| 2007/0166349 A1 | 7/2007 | White |
| 2007/0203584 A1* | 8/2007 | Bandyopadhyay ....... A61F 2/28 623/23.5 |
| 2008/0288083 A1 | 11/2008 | Axelsson et al. |
| 2009/0177287 A1 | 7/2009 | Sala et al. |
| 2010/0021865 A1 | 1/2010 | Uckelmann et al. |
| 2010/0137990 A1 | 6/2010 | Apatsidis et al. |
| 2010/0167020 A1 | 7/2010 | Jones et al. |
| 2011/0014081 A1 | 1/2011 | Jones et al. |
| 2011/0035020 A1 | 2/2011 | Laughner et al. |
| 2011/0190904 A1 | 8/2011 | Lechmann et al. |
| 2012/0064290 A1 | 3/2012 | Esat et al. |
| 2012/0308837 A1 | 12/2012 | Schlechtriemen et al. |
| 2012/0310365 A1 | 12/2012 | Chaput et al. |
| 2013/0030544 A1 | 1/2013 | Studer |
| 2013/0204384 A1 | 8/2013 | Hensley et al. |
| 2013/0264749 A1 | 10/2013 | Jones et al. |
| 2013/0282135 A1 | 10/2013 | Sun et al. |
| 2014/0025181 A1 | 1/2014 | Vanasse et al. |
| 2014/0106144 A1 | 4/2014 | Wong |

FOREIGN PATENT DOCUMENTS

| | | |
|---|---|---|
| WO | 2013126407 | 8/2013 |
| WO | 2013167904 | 11/2013 |
| WO | 2014028505 | 2/2014 |
| WO | 2014154901 | 10/2014 |
| WO | 2015132325 | 9/2015 |

OTHER PUBLICATIONS

Eurocoating, "Additive Manufacturing: long-term specialist expertise in manufacturing implantable devices" Additive Manufacturing, 2008, Eurocoating spa, Trento Italy, www.eurocoating.it.
E-Manufacturing Solutions, "Additive Manufacturing in the Medical Field", Medical, Mar. 2013, e-Manufacturing Solutions, Krailling/Munich Germany, www.eos.info.
Layerwise, "Medical Applications", LayerWise, 2012, Belgium, www.layerwise.com, www.dentwise.eu.
ipmd.net, "Powder Metallurgy Review", 2012, ipmd.net, pp. 1-32, www.ipmd.net.

* cited by examiner

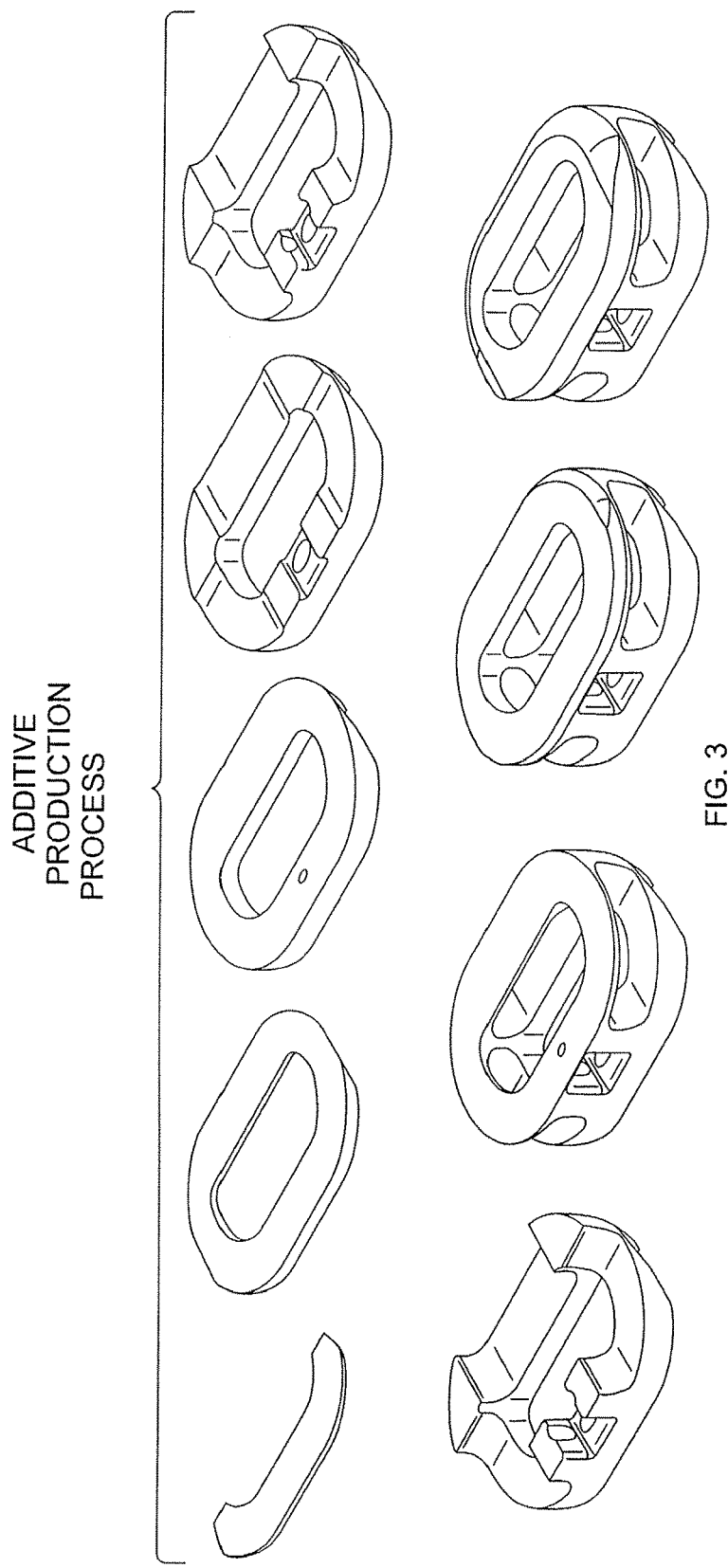

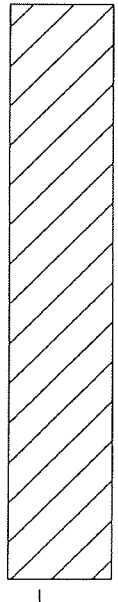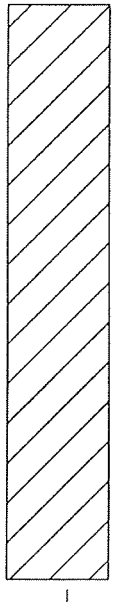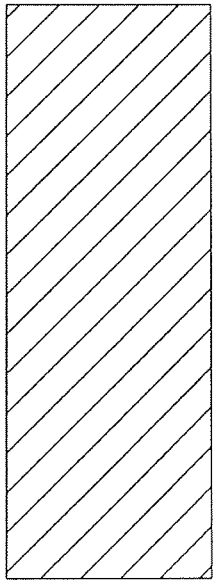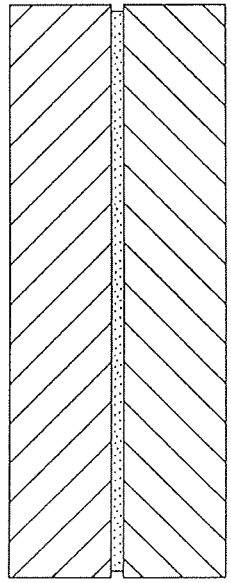

ADDITIVE AND SUBTRACTIVE MANUFACTURING PROCESS FOR PRODUCING IMPLANTS WITH HOMOGENEOUS BODY SUBSTANTIALLY FREE OF PORES AND INCLUSIONS

CROSS REFERENCE TO RELATED APPLICATIONS

This application claims priority to U.S. Patent Application No. 62/002,243 filed May 23, 2014, the contents of which are incorporated by reference herein, in their entirety and for all purposes.

FIELD OF THE INVENTION

The invention relates generally to combination additive-subtractive manufacturing methods for fabricating medical implants that, though produced in layers, have a homogeneous body and unitary crystal structure and are substantially free of pores and substantially free of inclusions, as well as implants prepared from these processes. The medical implants are well-suited for integration with bone, including through a bone growth-inducing surface topography produced by the subtractive manufacturing techniques.

BACKGROUND OF THE INVENTION

Various publications, including patents, published applications, technical articles and scholarly articles are cited throughout the specification. Each of these cited publications is incorporated by reference herein, in its entirety and for all purposes.

Orthopedic implants can be manufactured using conventional subtractive methods; milling, turning, drilling or sawing. They can also be produced using additive methods where materials in crystal or granular form are melted by energy sources and layered or applied while liquid to each other to form growing structures. These additive methods as a result, leave porosities within the bulk structure that are believed to establish pathways for bone ingrowth toward facilitating integration and fusion.

Bone fusion is enhanced by fibrous tissue formation that occurs after implantation and is loaded due to patient activity. In conventional implants, the implant material includes pores and openings of various sizes and shapes, and many are specifically manufactured to have pathways or open structures intentionally built in to allow for bone growth through the openings. One limitation of pores, however, is that the loads do not follow the often tortuous pathways and channels much beyond the opening of the porous structure and, therefore, bone growth through load-induced tensile and compressive forces is linear and the benefits are only realized for short distances into the structure. This results in the porous structure actually not allowing for the bone formation to penetrate through the implant structure.

In addition, as with any contact surface, the presence of pores and openings necessarily reduces the surface area available for contact and frictional stabilization. In fact, initial bone attachment is reduced in proportion to the amount of the porosity of the material. Moreover, if the resulting structures are too small in size such that the loads imparted on the bone by the implant device exceed the strength of the bone cells, the cells begin to remodel as a result of stress-induced necrosis which is a natural healing property of bones.

SUMMARY OF THE INVENTION

The invention features methods for producing an implant substantially free of pores and inclusions, which is substantially homogenous and comprises a substantially unitary crystal structure in the materials used to produce the implant, and which has one or more bioactive surfaces. In general, the methods comprise two categories of production, an additive manufacturing process to produce the implant body, and a refinement process to produce the one or more bioactive surfaces. The refinement process may be additive or subtractive.

In some aspects, the additive manufacturing process comprises substantially completely melting granules, particles, or powder of a material to form a molten material, depositing the molten material onto a substrate to form a first layer of the implant, then depositing the molten material onto the first layer of the implant to form the next layer of the implant, then depositing the molten material onto the next layer of the implant to form a subsequent layer of the implant, and repeating this depositing step until the implant body is completed. After the first layer of the implant is deposited, deposition of the next layer preferably partially melts the first layer onto which the molten material is deposited, thereby producing a substantially homogenous and substantially unitary crystal structure between the first layer and the next layer. After the next layer of the implant is deposited, deposition of the subsequent layer preferably partially melts the next (i.e., the previously formed) layer onto which the molten material is deposited, thereby producing a substantially homogenous and substantially unitary crystal structure between the next (i.e., the previously formed) layer and the subsequent layer (i.e., the layer being deposited).

Optionally, the method may comprise at least partially remelting one or more surfaces of the implant body to smooth the one or more partially remelted surfaces. It is preferred that the method does not include remelting or compressing the implant for purposes of homogenizing the layers (e.g., eliminating structural boundaries between the layers), but at least partially remelting of the implant surfaces for purposes of smoothing the surface is distinct from remelting for homogenization. Thus, the method may include the former (smoothing remelting), and preferably excludes the latter (homogenization remelting).

In preferred aspects, the refinement process is subtractive. In more preferred aspects, the refinement process comprises etching, abrasive blasting, or partially melting one or more surfaces of the implant to form macro structures and micro structures in the one or more surfaces, and thereafter, etching at least some of these same one or more surfaces of the implant to form nano structures in the one or more surfaces. The macro structures, micro structures, and nano structures together comprise the bioactive surface.

Following completion of both the additive and refinement processes of the method, the method produces an implant substantially free of pores and inclusions and having one or more bioactive surfaces. The implant body is substantially homogenous and comprises a substantially unitary crystal structure among the materials used to produce the implant, particularly among each adjacent deposited layer.

In preferred aspects, the material is a metal, but may also be a plastic or polymer, or a composite of a polymer and a metal. The metal may comprise titanium, or an alloy of titanium such as nitinol, or aluminum and vanadium alloys of titanium.

Selective laser melting may be used to substantially completely melt the granules, particles, or powder of the material. Electron beam melting may be used to substantially completely melt the raw material, which may be in the form of wires, bars, rods, granules, particles, or powder of the material.

The etching steps of the method are preferably carried out using an acid. In order to protect surfaces of the implant for which no etching is desired, the method may optionally comprise masking one or more surfaces on the implant. Whether or not masking is employed, the etching comprises immersing the implant in an acid solution for a period of time sufficient to form the macro structures and the micro structures in unmasked surfaces. The acid solution may comprise a mixture of nitric acid and hydrofluoric acid. The etching steps may comprise immersing the implant in a first acid solution and then a second acid solution, each immersion being for a period of time sufficient to form the macro structures and the micro structures in the unmasked surfaces. In such aspects, the first acid solution may comprise hydrofluoric acid and the second acid solution may comprise hydrochloric acid and sulfuric acid. The average depth of the etching may be about 0.5 mm below the plane of non-etched surfaces.

In addition to or in lieu of acid etching, the refinement process may comprise mechanically etching the one or more surfaces of the implant to form macro structures and micro structures in the one or more surfaces. Mechanically etching may comprise blasting or laser etching in some aspects. The average depth of the etching may be about 0.5 mm below the plane of non-etched surfaces.

The re-etching step may comprise immersing the implant in an aqueous acid solution for a period of time sufficient to form the nano structures. The aqueous acid solution may be heated.

The macro structures produced according to the refinement process may comprise an amplitude of about 20 microns to about 200 microns from the peak to the mean line, a peak-to-valley height of about 40 microns to about 500 microns, and a spacing of about 400 microns to about 2000 microns between macro features. The micro structures produced according to the refinement process may comprise an amplitude of about 1 micron to about 20 microns from the peak to the mean line, a peak-to-valley height of about 2 microns to about 40 microns, and a spacing of about 20 microns to about 400 microns between micro features. The nano structures produced according to the refinement process may comprise an amplitude of about 0.01 microns to about 1 micron from the peak to the mean line, a peak-to-valley height of about 0.2 microns to about 2 microns, and a spacing of about 0.5 microns to about 20 microns between nano features.

An implant produced according to the methods is within the scope of the invention. Preferably, the implant is substantially free of pores and inclusions. Preferably the implant is substantially free of pores. In aspects where pores are nevertheless present, for example, where such pores cannot be completely eliminated, but are minimized to at least a substantially free level, such pores have a minimal depth, are substantially vertical, and have substantially no non-vertical branches or off-shoots. The macro structures, micro structures, and nano structures are not pores or inclusions, and the refinement process that produces such structures does not produce pores or inclusions. The macro structures, micro structures, and nano structures may enhance bone growth or bone fusion relative to an implant of the same type in which such structures are not present.

BRIEF DESCRIPTION OF THE DRAWINGS

FIG. 3 shows an example of an additive process according to the invention in which layers are homogenous and without demarcations and seams between layers;

FIG. 5A shows a representation of different grain directions between successive layers prepared according to a traditional melt-layering process;

FIG. 5B shows a representation of the same grain direction between successive layers prepared according to the additive layering process of the invention, for example, as one layer is being actively laid on top of the lower layer;

FIG. 5C shows a representation of layers homogenous with each other, and substantially unitary in terms of the material crystal structure, for example, after one layer has been laid on top of a lower layer;

DETAILED DESCRIPTION OF THE INVENTION

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The terms "subject" or "patient" are used interchangeably. A subject may be any animal, including mammals such as companion animals, laboratory animals, and non-human primates. Human beings are preferred.

Figure 1:
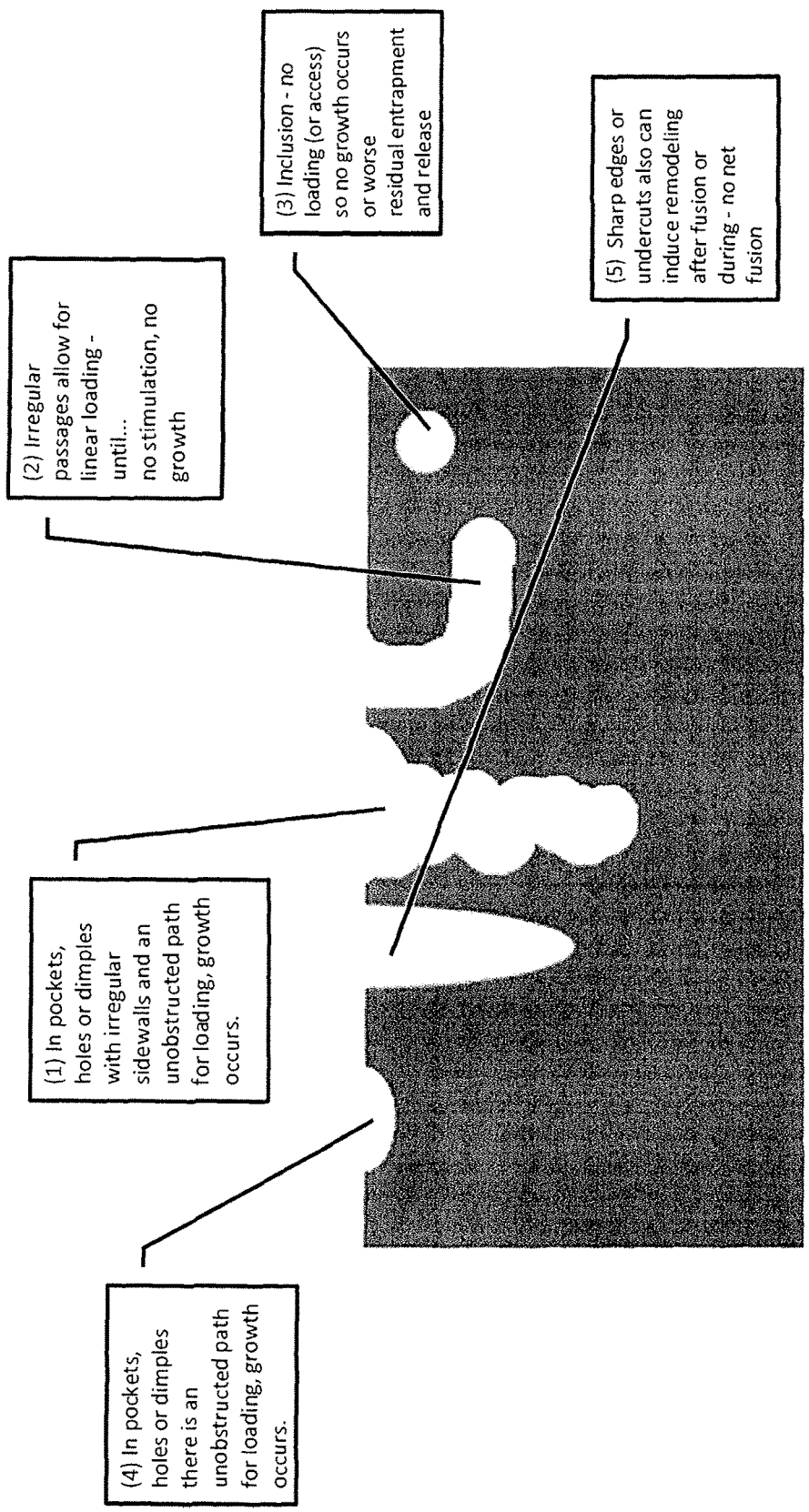
FIG. 1 shows a cartoon of pore structures that are present at or near the surface of metal implants. Part (1) illustrates a pore with irregularly shaped sidewalls, which are believed to induce bone remodeling after fusion or during fusion, such that no net bone fusion occurs in such pores. Part (2) illustrates a tunnel-like pore having non-vertical passageways in which it is believed that no loading and bone growth stimulation occurs. Part (3) illustrates an inclusion, with no access or loading possible such that no bone growth can occur. Part (4) illustrates a dimple with minimal depth. Part (5) illustrates a pocket with greater depth. The sharp edges surrounding the entry of the dimple or pocket at the junction with the top surface are believed to induce bone remodeling after fusion or during fusion, which may reduce optimal bone regrowth and implant integration.

It is believed that non-porous structures with textured surfaces stimulate bone growth and bone fusion, and enhance implant integration, and that load forces from compression and tension stimulate bone growth (FIG. 1). Accordingly, it is desired that the surface texture of metallic implants is intentionally designed, including the texture-feature density and depth, for stimulating biologic activity on the surface of the implant, and works in concert with the biologic loading of the device. It is further desirable to eliminate pores and inclusions within the implant material. Accordingly, the invention features processes for preparing implants having a substantially homogeneous body that has substantially no pores and/or substantially no inclusions. The crystal structure of the materials used to produce the substantially homogenous body is also substantially uniform. The implants so prepared may, in some aspects, have a minimal amount of pores, but such pores have a minimal depth and are substantially vertical, with substantially no non-vertical branches or off-shoots, with substantially no inclusions, and with no communication with or connection to other pores. Implants produced by such processes are also provided.

In general, implant fabrication to substantially reduce, minimize, or eliminate pores and inclusions comprises the basic steps of producing the implant body through an additive manufacturing process, and then refining one or more surfaces of the implant body to produce a bone growth-stimulating bioactive surface topography. The bone growth-stimulating surface topography facilitates osteointegration of the implant with the surrounding living bone once the implant is implanted within the body.

In some aspects, implant fabrication begins with engineering and designing the implant and its geometry, dimensions, and structural features. The implant may comprise, for example, a top surface, a bottom surface, at least one posterior side surface, at least one anterior side surface, and at least one lateral side surface. The implant may comprise flat, round, regular, and/or irregular surfaces. The implant may comprise any suitable shape, which shape may depend, for example, on the intended implantation location. The implant may, for example, comprise an implant for replacing an intervertebral disc, or for replacing a spinal motion segment. The implant may also comprise a joint implant, for example, an implant for the knee, shoulder, elbow, or pelvis. The implant may comprise any implant that, when implanted, is in contact with at least one or is in between two or more bones, and which is intended to induce fusion or physical joining of the separate bones (e.g., finger joints, ankle joints), or to facilitate rejoinder of broken bones, including bone screws, intermedulary shafts, rods, and plates. The implant may be used to replace, repair, brace, or supplement any bone in the body. In highly preferred embodiments, the implant is intended for integration with the surrounding bone. Implant engineering and design may be computer assisted.

It is preferred that implant fabrication comprises an additive manufacturing process. 3-D printing may be part of the additive manufacturing process. It is more preferred that such an additive process does not include any remelting, sintering, or compressing steps for purposes of homogenizing layers, such remelting or compressing steps occurring either between layer deposition steps or following completion of the bulk structure. For example, typical additive processes using granules, powders, or particles require a second step, generally after layering to complete the bulk structure, which second step attempts to reduce or compress internal porosities inherent in items produced by the initial layering process. This second step includes re-heating the implant such that the whole body, or at least a significant portion of the body is partially re-melted for homogenizing each layer, i.e., removing structural boundaries between each layer (e.g., FIG. 2) such that each layer is essentially melded with adjacent layers. The re-heating is also often accompanied by compression of the partially re-melted implant body to enhance the homogenization. But such re-melting processes also carry the risk of damaging the structure of the material by mechanically fracturing it at the granular level. In some cases, remelting also results in a surface that does not have sufficient microscopic topographic features to support bone cell proliferation. For implants intended to induce, facilitate, supplement, or support bone integration it is believed that microscopic topographic features, though not pores, support bone growth and enhance bone fusion and implant osteointegration.

Figure 2:
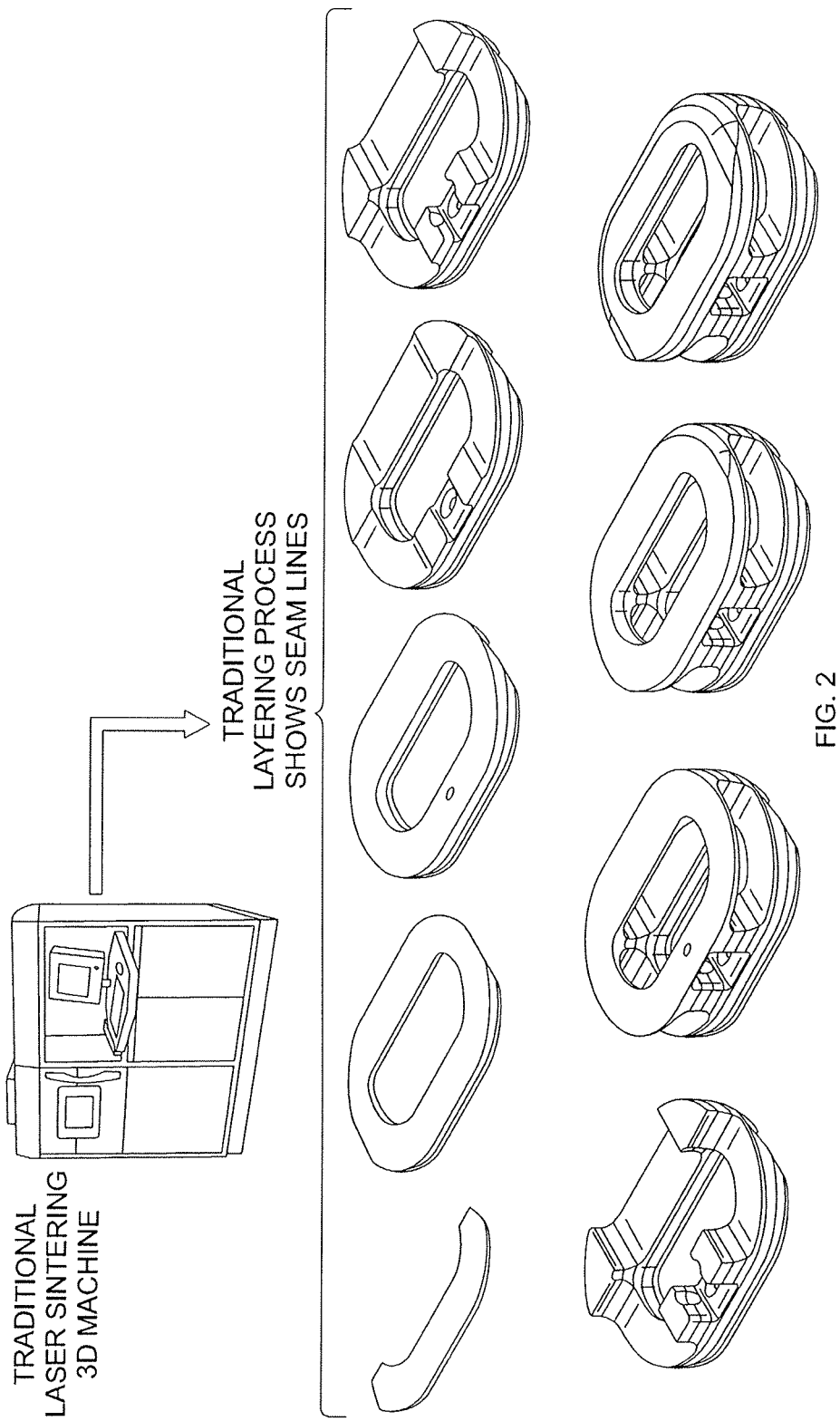
FIG. 2 shows an example of a traditional layering process in which demarcations and seams are created between layers.
Figure 4B:
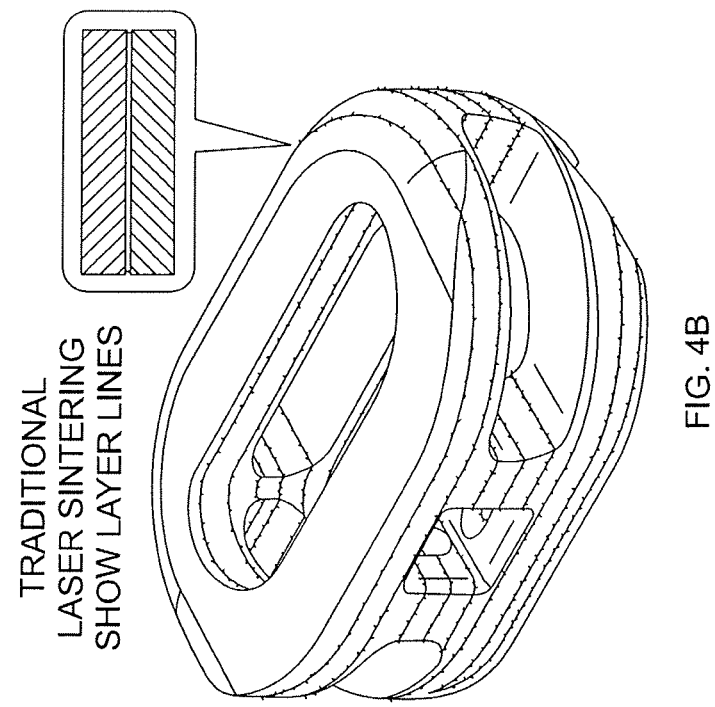
FIG. 4B shows a comparative example of an implant body prepared from a traditional 3D layering process in which demarcations and seams are created between layers; the inset box shows a close-up view of a representation of the junction between successive layers, indicating a potential variation in the grain direction between the layers.
Figure 4A:
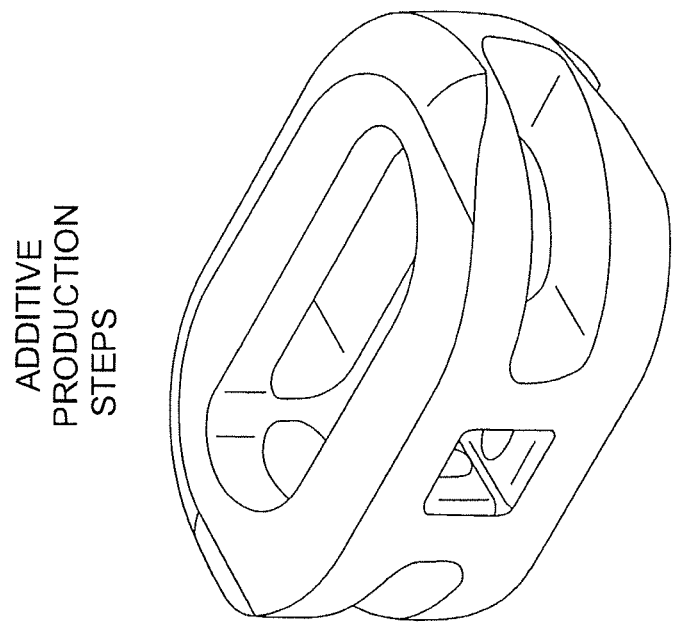
FIG. 4A shows an example of an implant body prepared from an additive process according to the invention in which the layers are homogenous and without demarcations and seams between layers.

Thus, the additive manufacturing process avoids the need to homogenize layers, as the process is accomplished in a way that does not produce structural boundaries, seams, or demarcations between layers (FIG. 2 and FIG. 4A, which may be compared, for example, with FIG. 4B). According to the additive manufacturing process, each layer is deposited in a way that it is homogenized and integral with the preceding layer, and other adjacent layers (FIG. 3 and FIG. 4A)

The implants may be prepared from any suitable material, including a metal, a polymer, a ceramic, bone, or any combination or composite thereof. Metal implants may comprise an alloy. Preferred metals include titanium and titanium alloys such as nitinol, aluminum and vanadium (e.g., 6-4) alloys of titanium, cobalt chromium alloys, as well as surgical grade steel. Preferred polymeric materials include polyetherether ketone (PEEK) and ultra-high molecular weight polyethylene (UHMWPE). Composites of metal and polymeric materials are also preferred in some aspects. Thus, the additive process may be used to fabricate implants comprised of such materials. Metal implants are highly preferred.

Additive processes may comprise melting a solid material, then successively layering the liquid/melt, first onto a substrate, and then onto a previous layer, and repeating until the implant is completed (FIG. 3). The solid material may comprise, for example, a bulk material in the form of a wire, bar, or rod, or in the form of a powder, or particles, or fragments, which is/are melted by an energy source, and deposited in liquid form onto the substrate. Deposition preferably takes place in an inert environment, for example, with low oxygen and/or in the presence of nitrogen and/or argon. Deposition preferably proceeds in layers, for example, by depositing a first layer of the implant body onto the substrate, then depositing a second layer of the implant body on top of the first layer, and so on until the entire implant body is assembled (FIG. 3). In some preferred aspects, a preceding layer (having just been deposited) has not substantially solidified prior to the successive layer being deposited thereon. In some preferred aspects, a preceding layer (having just been deposited) has at least partially solidified prior to the successive layer being deposited thereon such that the deposition of said successive layer, with the material being deposited in molten form, partially melts the preceding layer. In any case, each layer is thus homogenous with adjacent layers and the crystal structure of the material among adjacent layers is substantially continuous and unitary (FIG. 5C). The grain direction for each layer is preferably in the same direction (FIG. 5B and FIG. 5C), which may stand in contrast to certain traditional melt-layering processes in which grain direction may differ between or among layers (FIG. 5A, shown in opposite directions to illustrate the difference, though the direction of grains need not be directly opposed).

It is believed that an added benefit to this process of production is the lack of encapsulated porosities/inclusions, as well as segregated grain boundaries between the layers as the preceding layer is also melted when a second layer is added. The melt-laying of adjacent layers makes the adjacent layers homogenous with each other, substantially unitary in terms of the material crystal structure, and substantially pore-free. Accordingly, the implant so produced is also substantially homogenous, thereby lacking structural boundaries or demarcations between layers, has a substantially unitary crystal structure, and is substantially pore-free and inclusion-free on the whole.

The additive process may comprise sintering and/or melting of the granules, powders, or particles. The process preferably achieves substantially complete melting of the granules, powders, or particles such that the layer being deposited is comprised of substantially fully molten material, preferably metal. Suitable additive processes include, without limitation, selective laser sintering, including, for example, DMLS® (EOS GmbH), selective laser melting, including, for example, laserCUSING™ (Concept Laser Schutzrechtsverwaltungs GmbH), and electron beam melting. Thus, the energy source may comprise a laser or an electron beam, although any suitable technique for melting the material may be used.

The additive process is preferably coupled to a refining process that imparts bone growth- and/or fusion-enhancing features on surfaces of the implant. The refining process follows completion of the implant by the additive process. Such fusion-enhancing features may also facilitate osteointegration of the implant. Such features include a roughened, bioactive surface topography that is distinct from the pores, the latter being desirably avoided by the additive manufacturing process. The roughened, bioactive surface topography is also distinct from teeth, spikes, and ridges, and other bone-gripping macrostructures that are typically present on the surface of bone-contacting implants.

It is believed that the surface of an implant determines its ultimate ability to integrate into the surrounding living bone. Without being limited to any particular theory or mechanism of action, it is believed that the cumulative effects of at least implant composition, implant surface energy (including compression and tension), and implant surface roughness play a major role in the biological response to, and osteointegration of, an implant device. Thus, implant fixation may depend, at least in part, on the attachment and proliferation of osteoblasts and like-functioning cells upon the implant surface. Still further, it appears that these cells attach more readily to relatively rough surfaces rather than smooth surfaces. In this manner, a surface may be bioactive due to its ability to facilitate cellular attachment and osteointegration. Thus, a refining process imparts a roughened surface, preferably a bioactive roughened surface, onto the implant surface.

The refining process may include, for example, a form of a subtractive process that may include chemical etching, electrochemical etching, or mechanical etching. Mechanical etching includes, but is not limited to, exposure of select surfaces or the entire implant to photo etching, energy bombardment, abrasive blasting, plasma etching, laser etching, machining, drilling, grinding, peening, abrasive blasting (e.g., sand or grit blasting), or any combinations of such processes. Chemical etching may include, for example, exposure of select surfaces or the entire implant to a chemical such as an acid, with the acid etching the metal surfaces that come in contact with the acid. The refining process preferably does not impart pores into the surface of the implant, but preferably imparts a bioactive roughening into one or more desired surfaces of the implant.

The refining process may also include, for example, a form of an additive processes that is distinct from the additive process used to fabricate the implant body that is substantially pore-free (as above). Such a secondary additive process may include, for example, welding, thermal spraying, cold spraying, sputtering, and optical melt processes. The additive refining process imparts bioactive roughening into one or more desired surfaces of the implant without etching. Thus, for example, according to an additive refining process, particles, fibers, powders, and other pieces of material such as a metal are welded, thermal sprayed, cold sprayed, sputtered, or optically melted onto select surfaces or the entire implant.

The refining process may also include, for example, at least a partial remelting of at least the outer surfaces, including at least some superficial depth into the body, of the implant in order to smooth such surfaces. This remelting, which preferably takes place following the completion of the additive manufacturing process, is distinct from remelting of the implant for purposes of homogenizing adjacent layers. Select surfaces or the entire implant surfaces may be smoothed according to this refining process.

Chemical etching is a preferred subtractive refinement process. Acid etching comprises a preferred chemical etching process. For chemical etching, including acid etching, one or more surfaces of the implant may be masked to protect those surfaces from the chemical or acid, and exposed, unmasked surfaces that remain can then be etched. The protected surfaces may, for example, be those surfaces smoothed by a refinement remelting process as described in the preceding paragraph. The etching process may be repeated a number of times as necessitated by the amount and nature of the irregularities required for any particular application. Control of the strength of the etchant material, the temperature at which the etching process takes place, and the time allotted for the etching process allow fine control over the resulting surface produced by the process. The number of repetitions of the etching process can also be used to control the surface features.

By way of example, but not of limitation, an etchant mixture of nitric acid ($HNO_3$) and hydrofluoric (HF) acid may be repeatedly applied to a titanium surface to produce an average etch depth of about 0.53 mm. Surface roughness may be measured using a laser profilometer or other standard instrumentation. In another non-limiting example, chemical modification of the titanium implant surfaces can be achieved using HF and a combination of hydrochloric acid and sulfuric acid ($HCl/H_2SO_4$). In a dual acid etching process, the first exposure is to HF and the second is to $HCl/H_2SO_4$. Chemical acid etching alone of the titanium implant surface has the potential to greatly enhance osteointegration without adding particulate matter (e.g., hydroxyapatite) or embedding surface contaminants (e.g., grit particles).

The refining process produces a roughened, bioactive surface comprising macro-scale structural features, micro-scale structural features, and nano-scale structural features that collectively comprise a bioactive roughened surface. Macro structural features include relatively large dimensions, for example, dimensions measured in millimeters (mm) or microns (μm). Micro structural features include dimensions that are measured in microns (μm). Nano structural features include dimensions that are measured in nanometers (nm). Patterns of macro structural features, micro structural features, and/or nano structural features may be organized in regular and/or repeating patterns and optionally may overlap each other, or such features may be in irregular or random patterns, or repeating irregular patterns. Regular and repeating patterns are preferred.

It is believed that the roughened, bioactive surface helps to facilitate osteointegration (e.g., formation of a direct structural and functional interface between the artificial implant and living bone or soft tissue) with the surrounding living bone. Thus, implant fixation may depend, at least in part, on the stimulation and proliferation of bone modeling and forming cells, such as osteoclasts and osteoblasts and like-functioning cells upon the implant surface. It is believed that these cells attach more readily to relatively rough surfaces rather than smooth surfaces. In this manner, a surface may be bioactive due to its ability to stimulate cellular attachment and osteointegration.

The refined surfaces are composed of various sizes of features that, at the microscopic level, interact with the tissues and stimulate their natural remodeling and growth. At a larger scale these features perform the function of generating non-stressful friction that, when combined with a surgical technique that retains the most rigid cortical bone structures in the disc space, allow for a friction fit that does not abrade, chip, perforate, or compromise the critical endplate structures. The overlapping of the three feature sizes can be achieved using manufacturing processes that are completed sequentially and, therefore, do not remove or degrade the previous method.

The bioactive surface may be produced by the etching process, or the additive refinement process (e.g., deposition by thermal spraying, cold spraying, etc.). Before etching, the surface(s) to be etched may be cleaned and optionally blasted with an abrasive (e.g., alumina). Certain areas not to be etched may be masked. The masking and chemical etching may be repeated any number of times necessary to produce the desired pattern and etching depth. After the final etching process, the maskant may be removed and the part may be cleaned. The surface may also be passivated, for example, using an aqueous solution comprising nitric acid. The surface may be cleaned and rinsed with water.

In some aspects, the refinement process includes acid etching with a strong acid, such as hydrochloric acid (HCl), hydroiodic acid (HI), hydrobromic acid (HBr), hydrofluoric (HF), perchloric acid (HClO$_4$), nitric acid (HNO$_3$), and sulfuric acid (H$_2$SO$_4$). Preferably, the acid etching uses an aqueous solution comprising hydrochloric acid. The etching process may be repeated a number of times as necessitated by the amount and nature of the irregularities required for any particular application. Control of the strength of the etchant material, the temperature at which the etching process takes place, and the time allotted for the etching process allows fine control over the resulting surface produced by the process. The number of repetitions of the etching process can also be used to control the surface features.

By way of example, an etchant mixture of at least one of nitric acid and hydrofluoric acid may be repeatedly applied to a titanium surface to produce an average etch depth of about 0.5 mm. In another example, chemical modification of titanium can be achieved using at least one of hydrofluoric acid, hydrochloric acid, and sulfuric acid. In a dual acid etching process, for example, the first exposure is to hydrofluoric acid and the second is to a hydrochloric acid and sulfuric acid mixture. Chemical acid etching alone may enhance osteointegration without adding particulate matter (e.g., hydroxyapatite) or embedding surface contaminants (e.g., grit particles).

The macro features may be formed, for example, using three cut patterns. Specifically, a first cut pattern of the macro features may be formed. The "cut 1" features of the first cut pattern may cover about 20% of the total area of the surface, for example, leaving about 80% of the original surface remaining. The range of these percentages may be about ±20%, preferably ±10%, and more preferably about ±5%. The "cut 1" features of the first cut pattern do not have any undercuts. In some aspects, these "cut 1" features have the smallest diameter and greatest depth of the macro features that are formed during the sequential steps.

A second cut pattern of the macro features may be formed in the surface. Together, the "cut 1" features of the first cut pattern and the "cut 2" features of the second cut pattern may cover about 85% of the total area of the surface, for example, leaving about 15% of the original surface remaining. The range of these percentages may be about ±10% and preferably ±5%. In an embodiment of the invention, these "cut 2" features have both a diameter and a depth between those of the "cut 1" and "cut 3" features of the macro features that are formed during the first and third steps of the process of forming the macro features of the bioactive surface.

A third cut pattern of the macro features may be formed in the surface. Together, the "cut 1" features of the first cut pattern, the "cut 2" features of the second cut pattern, and the "cut 3" features of the third cut pattern may cover about 95% of the total area of the surface, for example, leaving about 5% of the original surface remaining. The range of these percentages may be about ±1%. In some aspects, these "cut 3" features may have the largest diameter and least depth of the macro features that are formed during the sequential process steps.

After the macro features are formed, additional refinement steps may be sequentially applied, in turn, to form the micro surface features (e.g., on the order of micrometers) of the bioactive surface. The micro features may also be formed from subtractive techniques (e.g., mechanical or chemical etching, for example) or additive techniques (e.g., deposition by thermal spraying, cold spraying, etc). Preferably, the micro features are also formed by subtractive techniques, and more preferably by acid etching.

After the macro features and micro features are formed, additional refinement process steps may be sequentially applied, in turn, to form the nano surface features (e.g., on the order of nanometers) of the bioactive surface. The nano features may also be formed from subtractive techniques (e.g., mechanical or chemical bulk removal, for example) or additive techniques (e.g., deposition by thermal spraying, cold spraying, etc). Preferably, the nano features are formed by subtractive techniques, more preferably by chemical etching, and even more preferably by acid etching.

In some aspects, portions of the implant surface, including portions of the surface exposed by the macro and micro steps described above, may be exposed to additional chemical etching in order to form the nano structural features. In an exemplary embodiment, the nano process also includes an acid etching, with a strong or weak acid, such as hydrochloric acid (HCl), hydroiodic acid (HI), hydrobromic acid (HBr), hydrofluoric acid (HF), perchloric acid (HClO$_4$), nitric acid (HNO$_3$), or sulfuric acid (H$_2$SO$_4$). The acid etching process for the nano step is preferably less aggressive than the acid etching process in the macro or micro steps. In other words, a less acidic, mild, or more diluted acid may be selected. In an exemplary embodiment, the nano features are created, at least partially, with an aqueous hydrochloric acid etching step.

As an example, the nano features (or (additional) micro features) may be formed by preparing an acid solution comprising hydrochloric acid, water, and titanium; applying the acid solution to the surface; removing the acid solution by rinsing with water; and heating and subsequently cooling the surface.

The acid solution may be prepared using any suitable techniques known in the art. For example, the acid solution may be prepared by combining hydrochloric acid and water, simultaneously or sequentially. The aqueous hydrochloric acid solution may optionally be heated, for example, to a temperature of about 150-250° F. (66-121° C.), preferably about 200-210° F. (93-99° C.), and most preferably about 205° F. (96° C.). The titanium may be seeded (e.g., added) in the aqueous hydrochloric acid solution or may already be present from titanium previously removed from at least one surface of the implant, for example, in a continuous manufacturing process. The solution may optionally be cooled. The acid solution may comprise a concentration of 20-40% hydrochloric acid, preferably about 25-31% hydrochloric acid, and more preferably about 28% hydrochloric acid, based on the total weight of the solution.

It is contemplated that the nano features may also be created by the abrasive or grit blasting, for example, as described for the micro processing step. Patterns may be organized in regular repeating patterns and optionally overlap each other. The nano features may also be achieved by tumble finishing (e.g., tumbling). The tumbling process may be wet (e.g., with a lubricant) or dry. After the nano features are formed, it is possible that less than about 1% of the original surface remains.

Any or each of the steps, including the macro, micro, or nano processing steps, may be accompanied by a cleaning step. In addition, the part may be cleaned once the processing steps are complete. For example, the part may be washed in an aqueous environment under agitation and heat with or without a detergent. Following washing, the part may be dried, for example with hot air, heating in a dry oven, or both.

The process steps described in this document can be adjusted to create a mixture of depths, diameters, feature sizes, and other geometries suitable for a particular implant application. The orientation of the pattern of features can also be adjusted. Such flexibility is desirable, especially because the ultimate pattern of the bioactive surface should be oriented in opposition to the biologic forces that may be applied against the implant upon implantation, and to the insertion direction.

Several separate parameters can be used to characterize the surface roughness. Among those parameters are the average amplitude, Ra; the maximum peak-to-valley height, Rmax; and the mean spacing, Sm. Surface roughness may be measured using a laser profilometer or other standard instrumentation.

In addition to the parameters Ra, Rmax, and Sm mentioned above, at least two other parameters can be used to characterize the roughness of an implant surface. In summary, the five parameters are: (1) average amplitude, Ra; (2) average peak-to-valley roughness, Rz; (3) maximum peak-to-valley height, Rmax; (4) total peak-to-valley of waviness profile, Wt; and (5) mean spacing, Sm.

Figure 6:
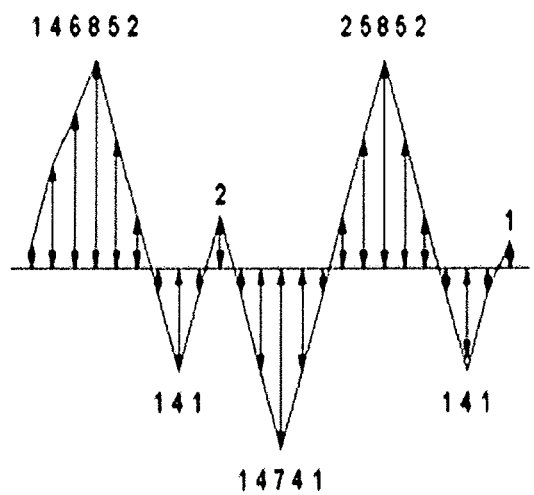
FIG. 6 graphically represents the average amplitude, Ra, of macro-, micro-, or nano-scale surface features and structures.

Average Amplitude Ra. Ra comprises an arithmetic average height. Mathematically, Ra may be computed as the average distance between each roughness profile point and the mean line. In FIG. 6, the average amplitude is the average length of the arrows.

In mathematical terms, this process can be represented by the following Formula I:

$$Ra = \frac{1}{n}\sum_{i=1}^{n}|y_i|$$

Figure 7:
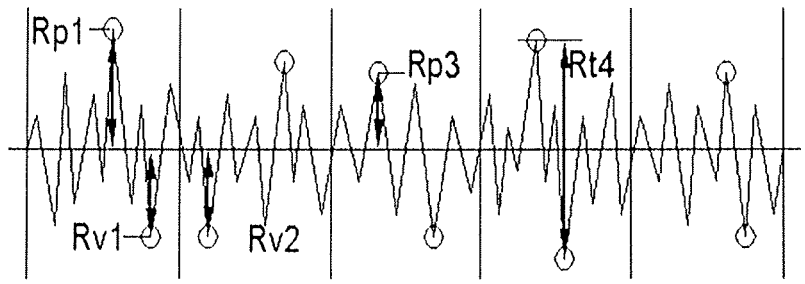
FIG. 7 graphically represents the average peak-to-valley roughness, Rz, of macro-, micro-, or nano-scale surface features and structures.

Average Peak-to-Valley Roughness Rz. The average peak-to-valley roughness, Rz, is defined by the ISO and ASME 1995 and later. Rz is based on one peak and one valley per sampling length. The RzDIN value is based on the determination of the peak-to-valley distance in each sampling length. These individual peak-to-valley distances are averaged, resulting in the RzDIN value, as illustrated in FIG. 7.

Figure 8:
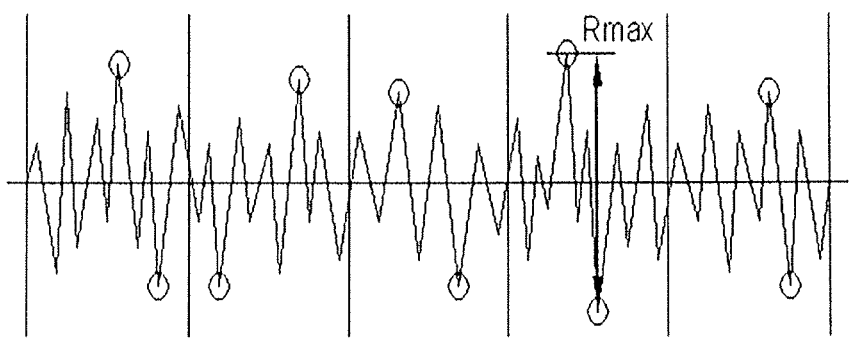
FIG. 8 graphically represents the maximum peak-to-valley height, Rmax, of macro-, micro-, or nano-scale surface features and structures.

Maximum Peak-to-Valley Height Rmax. The maximum peak-to-valley height, Rmax, comprises the maximum peak-to-valley distance in a single sampling length—as illustrated in FIG. 8.

Figure 9:
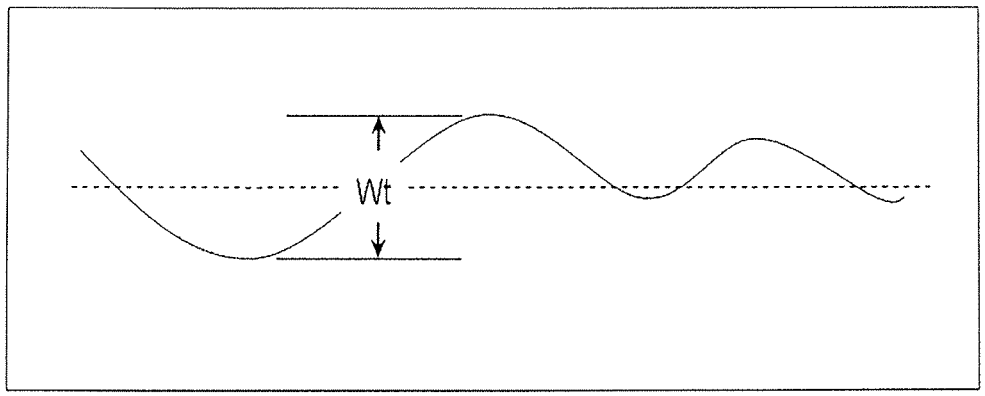
FIG. 9 graphically represents the total peak-to-valley of waviness of profile macro-, micro-, or nano-scale surface features and structure.

Total Peak-to-Valley of Waviness Profile Wt. The total peak-to-valley of waviness profile (over the entire assessment length) is illustrated in FIG. 9.

Figure 10:
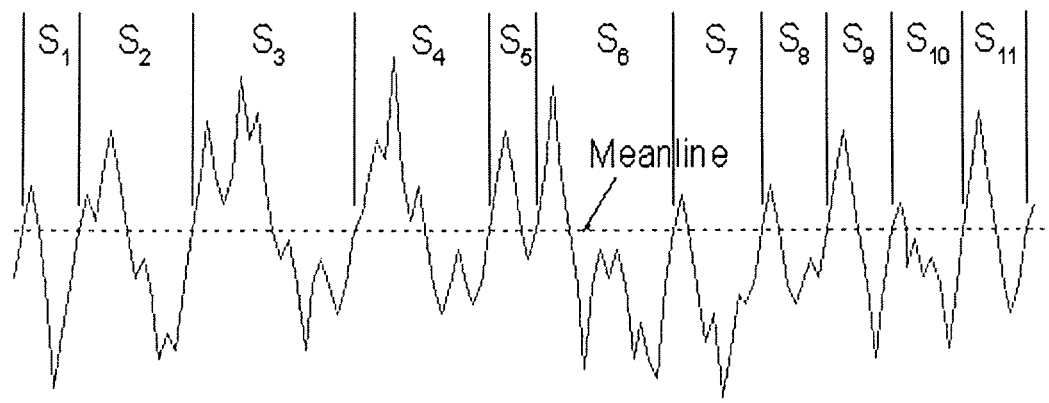
FIG. 10 graphically represents the mean spacing, Sm, of macro-, micro-, or nano-scale surface features and structures.

Mean Spacing Sm. The mean spacing, Sm, comprises the average spacing between positive mean line crossings. The distance between each positive (upward) mean line crossing is determined and the average value is calculated, as illustrated in FIG. 10.

The parameters Sm, Rmax, and Ra can be used to define the surface roughness following formation of each of the three types of features macro, micro, and nano. Such data are provided in Tables 1-3.

TABLE 1

Surface Feature Size and Roughness (Metric): Macro (µm)

|  | Size (Sm) | Depth (Rmax) | Roughness (Ra) |
|---|---|---|---|
| Max. | 2,000 | 500 | 200 |
| Min. | 400 | 40 | 20 |
| Avg. | 1,200 | 270 | 110 |

TABLE 2

Surface Feature Size and Roughness (Metric): Micro (µm)

|  | Size (Sm) | Depth (Rmax) | Roughness (Ra) |
|---|---|---|---|
| Max. | 400 | 40 | 20 |
| Min. | 20 | 2 | 1 |
| Avg. | 210 | 11 | 5.5 |

TABLE 3

Surface Feature Size and
Roughness (Metric): Nano (μm)

|      | Size (Sm) | Depth (Rmax) | Roughness (Ra) |
|------|-----------|--------------|----------------|
| Max. | 20        | 2            | 1              |
| Min. | 0.5       | 0.2          | 0.01           |
| Avg. | 10.25     | 1.1          | 0.505          |

The macro features for each of the three parameters may comprise the following preferred ranges (all measurements in microns). In some aspects, the macro mean spacing, Sm, is about 400 to about 2000 micrometers. More preferably, the macro mean spacing is about 750 to about 1750 micrometers, and more preferably, the macro mean spacing is about 1000 to about 1500 micrometers. In some aspects, the macro mean spacing is about 500 to about 1000 micrometers, about 600 to about 900 micrometers, about 700 to about 1000 micrometers, about 750 to about 1200 micrometers, about 800 to about 1300 micrometers, about 900 to about 1300 micrometers, about 1000 to about 1300 micrometers, about 1100 to about 1300 micrometers, about 1100 to about 1400 micrometers, about 1150 to about 1250 micrometers, about 1150 to about 1350 micrometers, about 1200 to about 1500 micrometers, or about 1200 to about 1400 micrometers. In some aspects, the macro peak-to-valley height, Rmax, is about 40 to about 500 micrometers. More preferably, the macro peak-to-valley height is about 150 to about 400 micrometers, and more preferably, about 250 to about 300 micrometers. In some aspects, the macro mean peak-to valley height is about 100 to about 450 micrometers, about 200 to about 400 micrometers, about 200 to about 300 micrometers, about 260 to about 280 micrometers, about 250 to about 350 micrometers, about 260 to about 320 micrometers, or about 270 to about 300 micrometers. In some aspects, the macro average amplitude, Ra, is about 20 to about 200 micrometers. More preferably, the macro average amplitude is about 50 to about 150 micrometers, and more preferably about 100 to about 120 micrometers. In some aspects, the macro average amplitude is about 80 to about 180 micrometers, about 90 to about 160 micrometers, about 90 to about 140 micrometers, about 100 to about 150 micrometers, about 100 to about 130 micrometers, about 105 to about 125 micrometers, or about 105 to about 115 micrometers.

The micro features for each of the three parameters may comprise the following preferred ranges (all measurements in microns). In some aspects, the micro mean spacing, Sm, is about 20 to about 400 micrometers. More preferably, the micro mean spacing is about 100 to about 300 micrometers, and more preferably, the macro mean spacing is about 200 to about 220 micrometers. In some aspects, the micro mean spacing is about 50 to about 350 micrometers, about 75 to about 350 micrometers, about 75 to about 300 micrometers, about 100 to about 325 micrometers, about 100 to about 250 micrometers, about 120 to about 220 micrometers, about 150 to about 250 micrometers, about 180 to about 240 micrometers, about 190 to about 230 micrometers, or about 205 to about 215 micrometers. In some aspects, the micro peak-to-valley height, Rmax, is about 2 to about 40 micrometers. More preferably, the micro peak-to-valley height is about 5 to about 25 micrometers, and more preferably, about 6 to about 16 micrometers. In some aspects, the micro mean peak-to valley height is about 0.5 to about 50 micrometers, about 1 to about 45 micrometers, about 1 to about 40 micrometers, about 1 to about 30 micrometers, about 1 to about 20 micrometers, about 1 to about 15 micrometers, about 2 to about 50 micrometers, about 2 to about 30 micrometers, about 2 to about 25 micrometers, about 3 to about 40 micrometers, about 3 to about 30 micrometers, about 4 to about 40 micrometers, about 4 to about 30 micrometers, about 5 to about 40 micrometers, about 5 to about 30 micrometers, about 7 to about 20 micrometers, about 7 to about 15 micrometers, about 8 to about 14 micrometers, or about 9 to about 13 micrometers. In some aspects, the micro average amplitude, Ra, is about 1 to about 20 micrometers. More preferably, the micro average amplitude is about 1 to about 10 micrometers, and more preferably about 3 to about 7 micrometers. In some aspects, the micro average amplitude is about 0.5 to about 30 micrometers, about 0.5 to about 25 micrometers, about 1 to about 15 micrometers, about 1 to about 10 micrometers, about 1 to about 9 micrometers, about 1 to about 7 micrometers, about 2 to about 9 micrometers, or about 4 to about 7 micrometers.

The nano features for each of the three parameters may comprise the following preferred ranges (all measurements in microns). In some aspects, the nano mean spacing, Sm, is about 0.5 to about 20 micrometers. More preferably, the nano mean spacing is about 5 to about 15 micrometers, and more preferably, the macro mean spacing is about 8 to about 12 micrometers. In some aspects, the nano mean spacing is about 0.1 to about 30 micrometers, about 0.25 to about 25 micrometers, about 0.5 to about 15 micrometers, about 0.5 to about 13 micrometers, about 1 to about 250 micrometers, about 1 to about 20 micrometers, about 1 to about 150 micrometers, about 2 to about 18 micrometers, about 2 to about 12 micrometers, about 7 to about 14 micrometers, or about 9 to about 11.5 micrometers. In some aspects, the nano peak-to-valley height, Rmax, is about 0.2 to about 2 micrometers. More preferably, the nano peak-to-valley height is about 0.5 to about 1.5 micrometers, and more preferably, about 0.8 to about 1.4 micrometers. In some aspects, the nano mean peak-to valley height is about 0.05 to about 5 micrometers, about 0.1 to about 3 micrometers, about 0.1 to about 2 micrometers, about 0.1 to about 1.5 micrometers, about 0.1 to about 0.4 micrometers, about 0.2 to about 3 micrometers, about 0.2 to about 2.5 micrometers, about 0.2 to about 1.8 micrometers, about 0.6 to about 1.6 micrometers, about 0.7 to about 1.5 micrometers, or about 0.9 to about 1.3 micrometers. In some aspects, the nano average amplitude, Ra, is about 0.01 to about 1 micrometers. More preferably, the nano average amplitude is about 0.05 to about 0.75 micrometers, and more preferably about 0.3 to about 0.7 micrometers. In some aspects, the nano average amplitude is about 0.005 to about 2 micrometers, about 0.005 to about 1.5 micrometers, about 0.01 to about 0.75 micrometers, about 0.01 to about 1.1 micrometers, about 0.01 to about 0.9 micrometers, about 0.01 to about 0.07 micrometers, about 0.025 to about 0.75 micrometers, or about 0.04 to about 0.6 micrometers.

The invention is not limited to the embodiments described and exemplified above, but is capable of variation and modification within the scope of the appended claims.

What is claimed:

1. A method for producing an implant substantially free of pores and inclusions and having one or more bioactive surfaces, comprising:
   (a) melting a metal source material to form a molten metal;
   (b) depositing the molten metal onto a substrate to form a layer of the implant;

(c) depositing the molten metal onto the previously formed layer of the implant to form the next layer of the implant, wherein depositing the molten metal according to this step partially melts the previously formed layer onto which the molten metal is deposited, thereby producing a substantially homogenous and substantially unitary crystal structure between the previously formed layer and the next layer;

(d) repeating step (c) until the implant is completed;

(e) optionally, partially remelting one or more surfaces of the implant to smooth the one or more surfaces;

(f) etching or partially melting one or more surfaces of the implant to form macro structures and micro structures in the one or more surfaces; and (g) after step (f), etching the one or more surfaces of the implant to form nano structures in the one or more surfaces, thereby producing an implant substantially free of pores and inclusions and having one or more bioactive surfaces, with the proviso that the method does not include remelting or compression of the implant to homogenize the layers.

2. The method of claim 1, wherein selective laser melting is used to melt the metal source material.

3. The method of claim 1, wherein electron beam melting is used to melt the metal source material.

4. The method of claim 1, wherein the implant is substantially homogenous.

5. The method of claim 1, wherein the metal comprises titanium or an alloy of titanium.

6. The method of claim 1, wherein the etching of step (f) comprises masking one or more surfaces on the implant, and then immersing the implant in an acid solution for a period of time sufficient to form the macro structures and the micro structures in the unmasked surfaces.

7. The method of claim 6, wherein the acid solution comprises a mixture of nitric acid and hydrofluoric acid.

8. The method of claim 1, wherein the etching of step (f) comprises masking one or more surfaces on the implant, and then immersing the implant in a first acid solution and then a second acid solution, each immersion being for a period of time sufficient to form the macro structures and the micro structures in the unmasked surfaces.

9. The method of claim 8, wherein the first acid solution comprises hydrofluoric acid and the second acid solution comprises hydrochloric acid and sulfuric acid.

10. The method of claim 6, wherein unmasked surfaces of the implant are etched to an average depth of about 0.5 mm below the plane of non-etched surfaces.

11. The method of claim 1, wherein the etching of step (f) comprises mechanically etching or laser etching the one or more surfaces of the implant to form macro structures and micro structures in the one or more surfaces.

12. The method of claim 11, wherein the etched surfaces of the implant are etched to an average depth of about 0.5 mm below the plane of non-etched surfaces.

13. The method of claim 1, wherein the re-etching of step (g) comprises immersing the implant in an aqueous add solution for a period of time sufficient to form the nano structures.

14. The method of claim 13, wherein the aqueous acid solution is heated.

15. The method of claim 1, wherein the macro structures comprise an amplitude of about 20 microns to about 200 microns from the peak to the mean line, a peak-to-valley height of about 40 microns to about 500 microns, and a spacing of about 400 microns to about 2000 microns between macro features.

16. The method of claim 1, wherein the micro structures comprise an amplitude of about 1 micron to about 20 microns from the peak to the mean line, a peak-to-valley height of about 2 microns to about 40 microns, and a spacing of about 20 microns to about 400 microns between micro features.

17. The method of claim 1, wherein the nano structures comprise an amplitude of about 0.01 microns to about 1 micron from the peak to the mean line, a peak-to-valley height of about 0.2 microns to about 2 microns, and a spacing of about 0.5 microns to about 20 microns between nano features.

18. The method of claim 1, wherein any surface pores on the implant have a minimal depth, are substantially vertical, and have substantially no non-vertical branches or offshoots.

19. The method of claim 1, wherein the implant is completely free of surface pores.

20. The method of claim 1, wherein the bioactive surface enhances bone growth or bone fusion relative to an implant of the same type in which a bioactive surface is not present.

21. The method of claim 1, wherein the implant comprises a replacement for an intervertebral disc, a spinal motion segment, or a joint.

22. The method of claim 1, wherein the metal source material comprises a metal wire, a metal bar, a metal rod, metal granules, metal particles, or metal powder.

23. The method of claim 8, wherein unmasked surfaces of the implant are etched to an average depth of about 0.5 mm below the plane of non-etched surfaces.

24. An implant substantially free of pores and inclusions and having one or more bioactive surfaces, which implant is produced by the method of claim 1.

* * * * *